United States Patent
Kim et al.

(10) Patent No.: US 11,922,624 B2
(45) Date of Patent: Mar. 5, 2024

(54) BRAIN LESION INFORMATION PROVISION DEVICE AND METHOD

(71) Applicant: JLK INC., Cheongju-si (KR)

(72) Inventors: Won Tae Kim, Suwon-si (KR); Shin Uk Kang, Seoul (KR); Myung Jae Lee, Seoul (KR); Dong Min Kim, Seoul (KR); Jin Seong Jang, Seoul (KR)

(73) Assignee: JLK INC., Cheongju-si (KR)

( * ) Notice: Subject to any disclaimer, the term of this patent is extended or adjusted under 35 U.S.C. 154(b) by 387 days.

(21) Appl. No.: 17/418,922

(22) PCT Filed: Dec. 27, 2019

(86) PCT No.: PCT/KR2019/018593
§ 371 (c)(1),
(2) Date: Jun. 28, 2021

(87) PCT Pub. No.: WO2020/139011
PCT Pub. Date: Jul. 2, 2020

(65) Prior Publication Data
US 2022/0114723 A1    Apr. 14, 2022

(30) Foreign Application Priority Data

Dec. 27, 2018  (KR) .......................... 10-2018-0171152

(51) Int. Cl.
*G06T 7/00* (2017.01)
*G06T 11/00* (2006.01)
*G16H 30/40* (2018.01)

(52) U.S. Cl.
CPC .......... *G06T 7/0012* (2013.01); *G06T 11/006* (2013.01); *G16H 30/40* (2018.01);
(Continued)

(58) Field of Classification Search
CPC ................. G06T 7/0012; G06T 11/006; G06T 2207/20081; G06T 2207/30016;
(Continued)

(56) References Cited

U.S. PATENT DOCUMENTS 9,042,626 B1 * 5/2015 Katsevich ............. G06T 11/006
382/131
11,410,317 B2 * 8/2022 Paul .......................... G06T 7/11
(Continued)

FOREIGN PATENT DOCUMENTS

KR     10-2015-0099384 A    8/2015
KR         10-1740464 B1    6/2017
(Continued)

*Primary Examiner* — Md K Talukder
(74) *Attorney, Agent, or Firm* — BROADVIEW IP LAW, PC

(57) ABSTRACT

An apparatus for providing brain lesion information based on an image includes a magnetic resonance angiography (MRA) provider configured to provide an environment capable of displaying 3D time-of-flight magnetic resonance angiography (3D TOF MRA) using user input, a brain lesion input unit configured to generate and manage a brain lesion image, a maximum intensity projection (MIP) converter configured to configure MIP image data including at least one image frame corresponding to a projection position of the brain lesion image, a noise remover configured to remove noise of brain lesion information and to configure corrected MIP image data, from which the noise is removed, and an MRA reconfiguration unit configured to reconfigure a corrected brain lesion image by back-projecting the corrected MIP image data.

10 Claims, 11 Drawing Sheets

(52) U.S. Cl.
CPC ............... *G06T 2207/20081* (2013.01); *G06T 2207/30016* (2013.01); *G06T 2207/30096* (2013.01)

(58) Field of Classification Search
CPC .......... G06T 2207/30096; G16H 30/40; G16H 50/20; G01R 33/5608; G01R 33/5635; A61B 5/0035; A61B 5/004; A61B 5/055
See application file for complete search history.

(56) References Cited

U.S. PATENT DOCUMENTS

2009/0274352 A1* 11/2009 Chang ................ G01R 33/5635
  382/130
2011/0213237 A1* 9/2011 Park ....................... A61B 5/055
  600/410
2020/0315455 A1* 10/2020 Lee ...................... A61B 5/4082
2022/0114723 A1* 4/2022 Kim ...................... G06T 7/0012

FOREIGN PATENT DOCUMENTS

| KR | 10-1754291 B1 | 7/2017 |
| KR | 10-1804699 B1 | 12/2017 |
| KR | 10-1996476 B1 | 7/2019 |

* cited by examiner

CORRECTED MIP IMAGE DATA

FIG. 5B
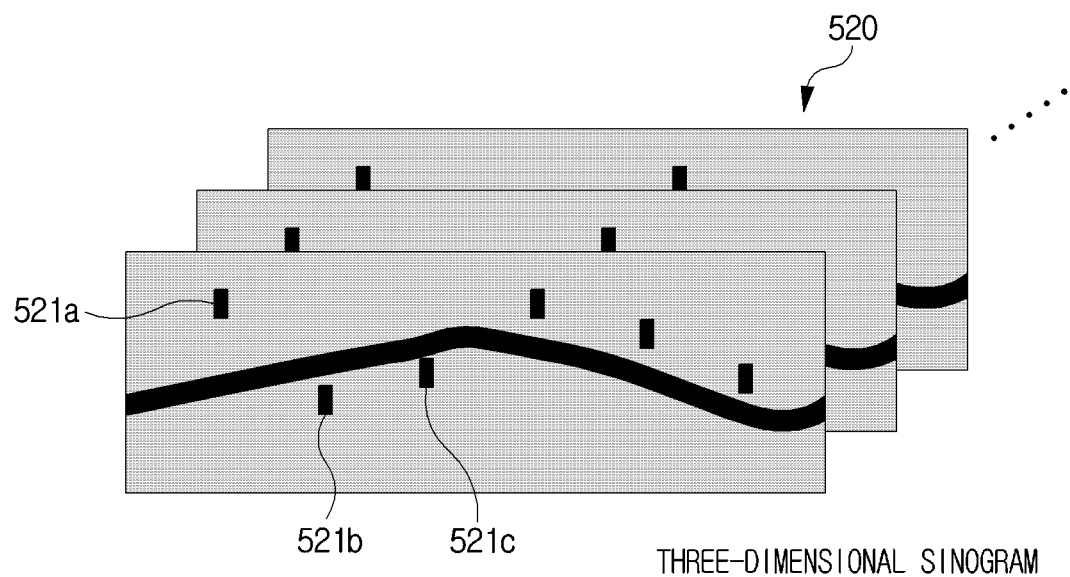
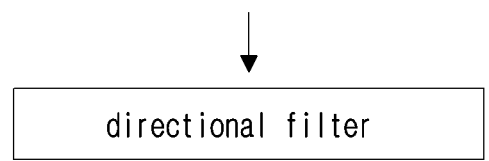
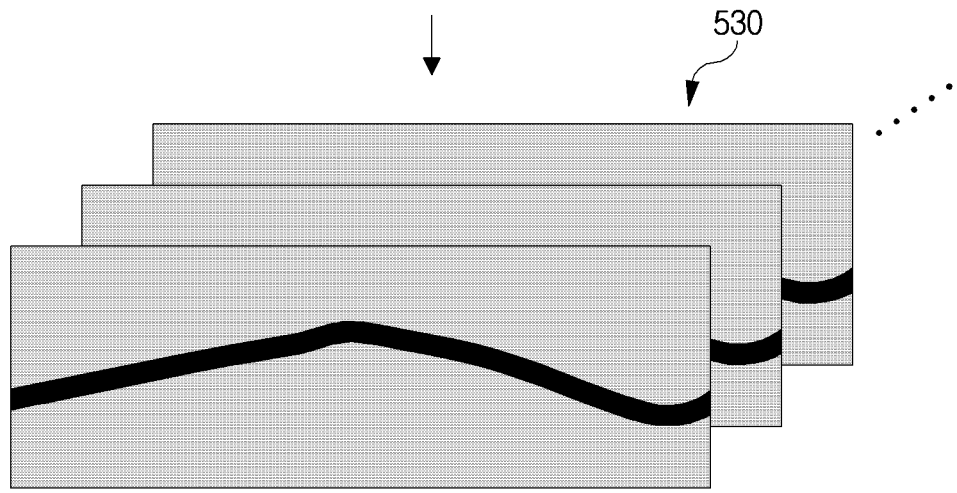

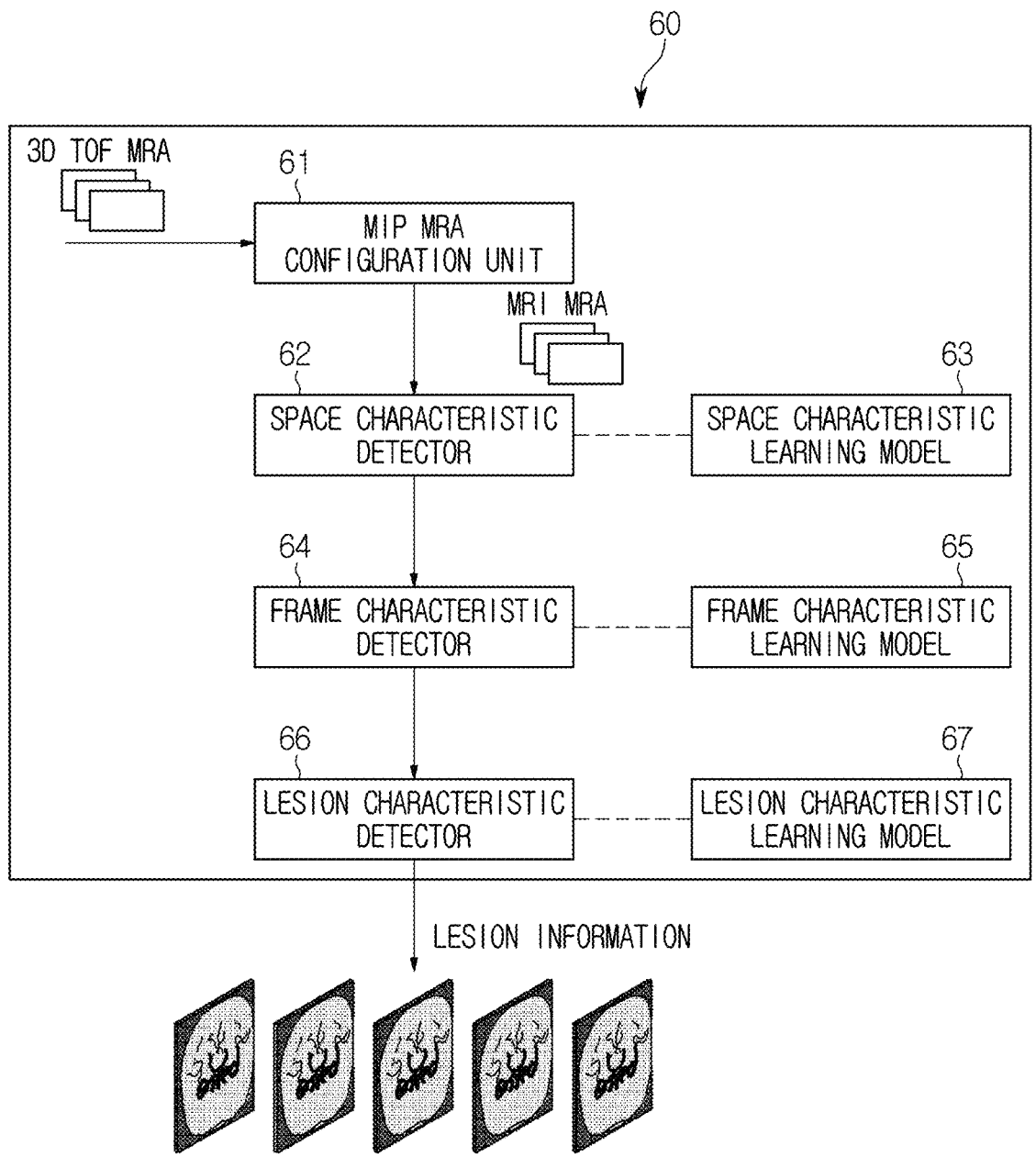

BRAIN LESION INFORMATION PROVISION DEVICE AND METHOD

TECHNICAL FIELD

The present disclosure relates to image processing technology, and, more particularly, to a method and apparatus for marking and providing detected or input brain lesion information on a three-dimensional brain image.

BACKGROUND ART

A medical imaging apparatus obtains an internal structure of a subject as an image. A medical image processing apparatus is a non-invasive test apparatus, which photographs, processes and displays a structural details of a body, internal tissues and flow of fluids to a user. A user (e.g., a doctor) may diagnose a patient's health condition and disease using a medical image output from the medical image processing apparatus.

Tissue is static, but a blood vessel has continuous circulation. Using such a characteristic difference, the blood vessel and the tissue are distinguished through an image. Using such characteristics, a 3D time of flight (TOF)-magnetic resonance angiography (MRA) apparatus is being used.

3D TOF MRA is to image a difference in relative magnetization occurring when circulating blood flow enters a static tissue, and is widely used to analyze a vascular disease, more particularly, cerebrovascular disease. The 3D TOF MRA simply displays only the vascular status of a subject (e.g., a patient) and does not directly display a brain lesion such as a cerebrovascular disease.

The user (e.g., a doctor) checks 3D TOF MRA and provides the patient with an area suspected of a brain lesion such as a cerebrovascular disease or uses 3D TOF MRA for future disease analysis or as a reference image during surgery. A brain lesion such as a cerebrovascular disease has a three-dimensional structure, but an area suspected of a brain lesion may not be directly displayed or marked on 3D TOF MRA.

DISCLOSURE

Technical Problem

A user (e.g., a doctor) directly displays or marks an area suspected of a brain lesion such as a cerebrovascular disease on 3D TOF MRA, and an apparatus capable of displaying an area marked by the user, that is, a brain lesion occurrence area, as a three-dimensional structure is required.

Furthermore, deep learning learns a very large amount of data and selects an answer with a highest probability based on a result of learning when new data is input. Since such deep learning may adaptively operate according to an image and automatically find characteristic factors in a process of learning a model based on data, attempts to utilize deep learning in the field of artificial intelligence are increasing recently.

In consideration of the forgoing, in order to construct a learning model using a medical image, a data set used for learning, for example, an image accurately marked with a disease occurrence area, is required. In particular, in order to accurately learn a brain lesion area using 3D TOF MRA, an image in which a brain lesion occurrence area is displayed in a three-dimensional structure is required.

An object of the present disclosure is to provide a method and apparatus capable of constructing a three-dimensional image accurately representing a brain lesion area detected using 3D TOF MRA in a three-dimensional structure.

Another object of the present disclosure is to provide a method and apparatus capable of accurately representing a brain lesion area on a three-dimensional image, by removing noise which may occur upon input.

The technical problems solved by the present disclosure are not limited to the above technical problems and other technical problems which are not described herein will become apparent to those skilled in the art from the following description.

Technical Solution

According to an aspect of the present disclosure, an apparatus for providing brain lesion information based on an image may include a magnetic resonance angiography (MRA) provider configured to provide an environment capable of displaying 3D time-of-flight magnetic resonance angiography (3D TOF MRA) using user input, a brain lesion input unit configured to annotate a brain lesion area and to generate and manage a brain lesion image by combining the annotated brain lesion area and the 3D TOF MRA, a maximum intensity projection (MIP) converter configured to configure MIP image data including at least one image frame corresponding to a projection position of the brain lesion image, a noise remover configured to remove noise of brain lesion information from the at least one image frame included in the MIP image data and to configure corrected MIP image data reflecting brain lesion information, from which the noise is removed, and an MRA reconfiguration unit configured to reconfigure a corrected brain lesion image by back-projecting the corrected MIP image data.

According to an aspect of the present disclosure, a method of, by an electronic apparatus, providing brain lesion information based on an image may include providing 3D time-of-flight magnetic resonance angiography (3D TOF MRA), annotating a brain lesion area and generating a brain lesion image by combining the annotated brain lesion area and the 3D TOF MRA, configuring maximum intensity projection (MIP) image data including at least one image frame corresponding to a projection position of the brain lesion image, removing noise of brain lesion information from the at least one image frame included in the MIP image data and configuring corrected MIP image data reflecting brain lesion information, from which the noise is removed, and reconfiguring a corrected brain lesion image by back-projecting the corrected MIP image data.

The features briefly summarized above with respect to the present disclosure are merely exemplary aspects of the detailed description below of the present disclosure, and do not limit the scope of the present disclosure.

Effects of Invention

According to the present disclosure, it is possible to provide a method and apparatus capable of constructing a three-dimensional image accurately representing a brain lesion area detected using 3D TOF MRA in a three-dimensional structure.

According to the present disclosure, it is possible to provide a method and apparatus capable of accurately representing a brain lesion area on a three-dimensional image, by removing noise which may occur upon input.

It will be appreciated by persons skilled in the art that that the effects that can be achieved through the present disclosure are not limited to what has been particularly described herein and other advantages of the present disclosure will be more clearly understood from the detailed description.

DESCRIPTION OF DRAWINGS

The above and other objects, features and other advantages of the present disclosure will be more clearly understood from the following detailed description taken in conjunction with the accompanying drawings, in which:

FIGS. 5a to 5c are views illustrating data processed by a noise remover provided in a brain lesion information provision apparatus according to an embodiment of the present disclosure;

FIG. 6 is a block diagram illustrating the configuration of a cerebrovascular disease detection apparatus provided in a brain lesion information provision apparatus according to an embodiment of the present disclosure;

MODE FOR INVENTION

Figure 1:
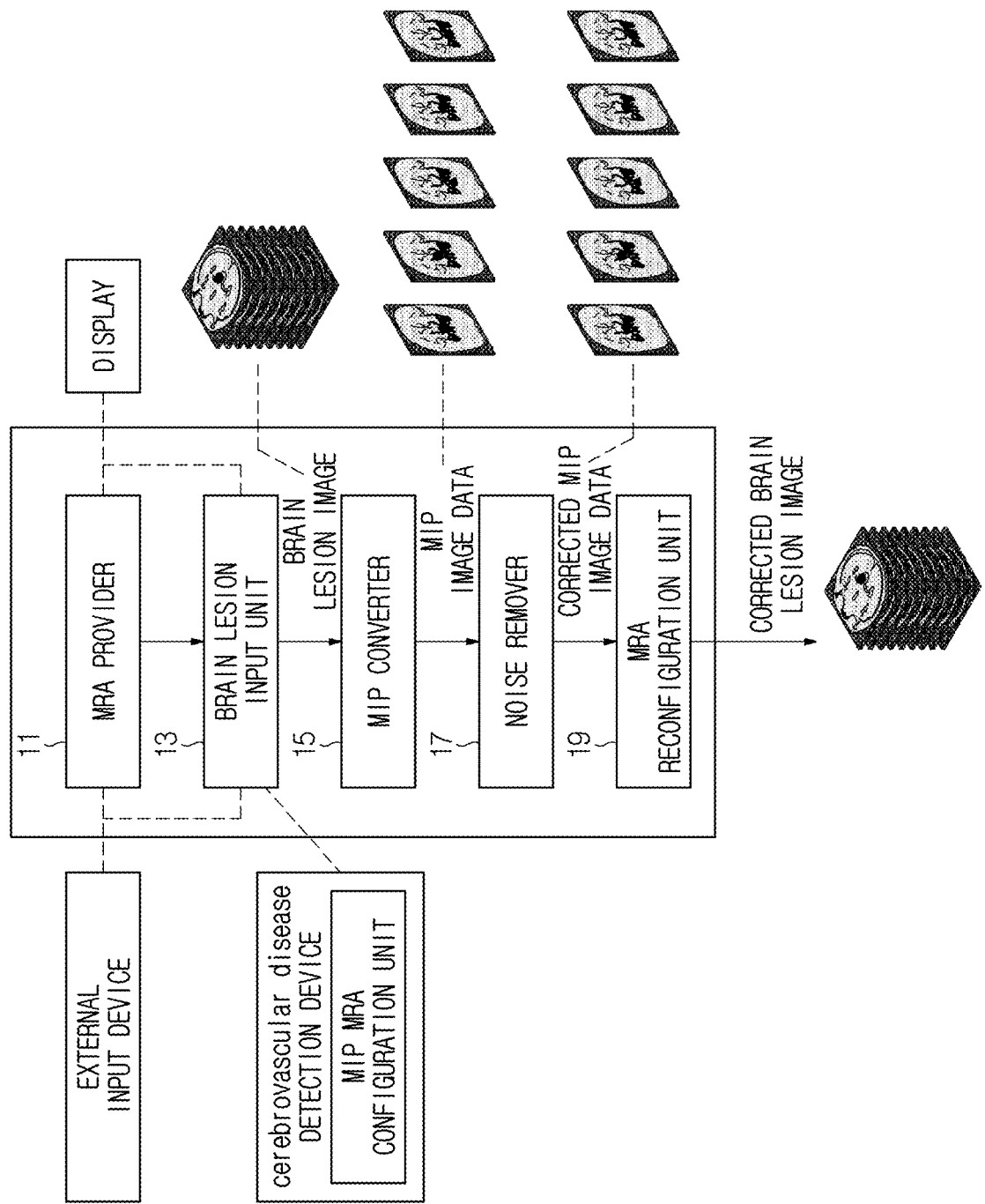
FIG. 1 is a block diagram illustrating the configuration of a brain lesion information provision apparatus according to an embodiment of the present disclosure.

Hereinbelow, exemplary embodiments of the present disclosure will be described in detail with reference to the accompanying drawings such that the present disclosure can be easily embodied by one of ordinary skill in the art to which this invention belongs. However, the present disclosure may be variously embodied, without being limited to the exemplary embodiments.

In the description of the present disclosure, the detailed descriptions of known constitutions or functions thereof may be omitted if they make the gist of the present disclosure unclear. Also, portions that are not related to the present disclosure are omitted in the drawings, and like reference numerals designate like elements.

In the present disclosure, when an element is referred to as being "coupled to", "combined with", or "connected to" another element, it may be connected directly to, combined directly with, or coupled directly to another element or be connected to, combined directly with, or coupled to another element, having the other element intervening therebetween. Also, it should be understood that when a component "includes" or "has" an element, unless there is another opposite description thereto, the component does not exclude another element but may further include the other element.

In the present disclosure, the terms "first", "second", etc. are only used to distinguish one element, from another element. Unless specifically stated otherwise, the terms "first", "second", etc. do not denote an order or importance. Therefore, a first element of an embodiment could be termed a second element of another embodiment without departing from the scope of the present disclosure. Similarly, a second element of an embodiment could also be termed a first element of another embodiment.

In the present disclosure, components that are distinguished from each other to clearly describe each feature do not necessarily denote that the components are separated. That is, a plurality of components may be integrated into one hardware or software unit, or one component may be distributed into a plurality of hardware or software units. Accordingly, even if not mentioned, the integrated or distributed embodiments are included in the scope of the present disclosure.

In the present disclosure, components described in various embodiments do not denote essential components, and some of the components may be optional. Accordingly, an embodiment that includes a subset of components described in another embodiment is included in the scope of the present disclosure. Also, an embodiment that includes the components described in the various embodiments and additional other components are included in the scope of the present disclosure.

FIG. 1 is a block diagram illustrating the configuration of a brain lesion information provision apparatus according to an embodiment of the present disclosure.

Referring to FIG. 1, the brain lesion information provision apparatus 10 may include an MRA provider 11, a brain lesion input unit 13, an MIP converter 15, a noise remover 17 and an MRA reconfiguration unit 19.

The MRA provider 11 may provide an environment capable of displaying 3D Time-of-flight magnetic resonance angiography (3D TOF MRA) using user input. 3D TOF MRA may be 3D MRA obtained by strongly measuring a signal of an area, in which a blood vessel is present, in a brain area. Since 3D TOF MRA is 3D data, the MRA provider 11 may check an area input by a user and set a projection position according to the checked area.

For example, the MRA provider 11 may be connected to an external input device such as a mouse device, a digitizer device or a touchscreen device and may check a signal input through the external input device. In addition, the MRA provider 11 may include a user interface and provide an input signal of the external input device through the user interface. Specifically, the user interface may be configured to check a projection position corresponding to an input area of the external input device and to display 3D TOF MRA appearing at a position corresponding thereto. In addition, the user interface may be configured to display MRA enlarged or reduced according to the input signal of the external input device.

The brain lesion input unit 13 may provide an environment capable of setting an area selected by a user as a brain lesion area while displaying 3D TOF MRA provided by the MRA provider 11.

Figure 2:
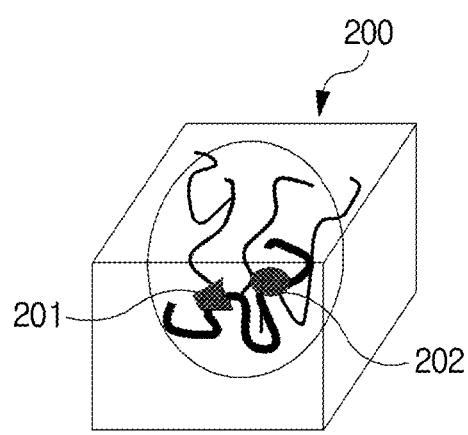
FIG. 2 is a view illustrating operation of inputting a brain lesion by a brain lesion information provision apparatus according to an embodiment of the present disclosure.

Specifically, the brain lesion input unit 13 may provide a user interface capable of outputting 3D TOF MRA 200 (see FIG. 2) on a display and receiving an area in which a brain lesion is present, that is, a brain lesion area, in the 3D TOF MRA. For example, the brain lesion input unit 13 may be connected through an external input device such as a mouse device, a digitizer device or a touchscreen device to output a predetermined indicator in an area designated by the external input device and to annotate an area selected by the external input device as brain lesion areas 201 and 202.

The brain lesion input unit 13 may store and manage the annotated brain lesion area as brain lesion information and, in particular, generate and manage a brain lesion image through combination with 3D MRA. The brain lesion image is based on 3D MRA, may be configured in a 3D form, and may be differently represented according to a projection position. Based on this, the MIP converter 15 may convert a 3D brain lesion image into at least one maximum intensity projection (MIP) image corresponding to a predetermined projection position and provide the converted MIP image.

For example, the MIP converter 15 may check the predetermined projection position and obtain an image frame corresponding to the checked projection position from the brain lesion image. In addition, the MIP converter 15 may configure MIP image data by combining a plurality of image frames obtained through the above-described operation.

Figure 3:
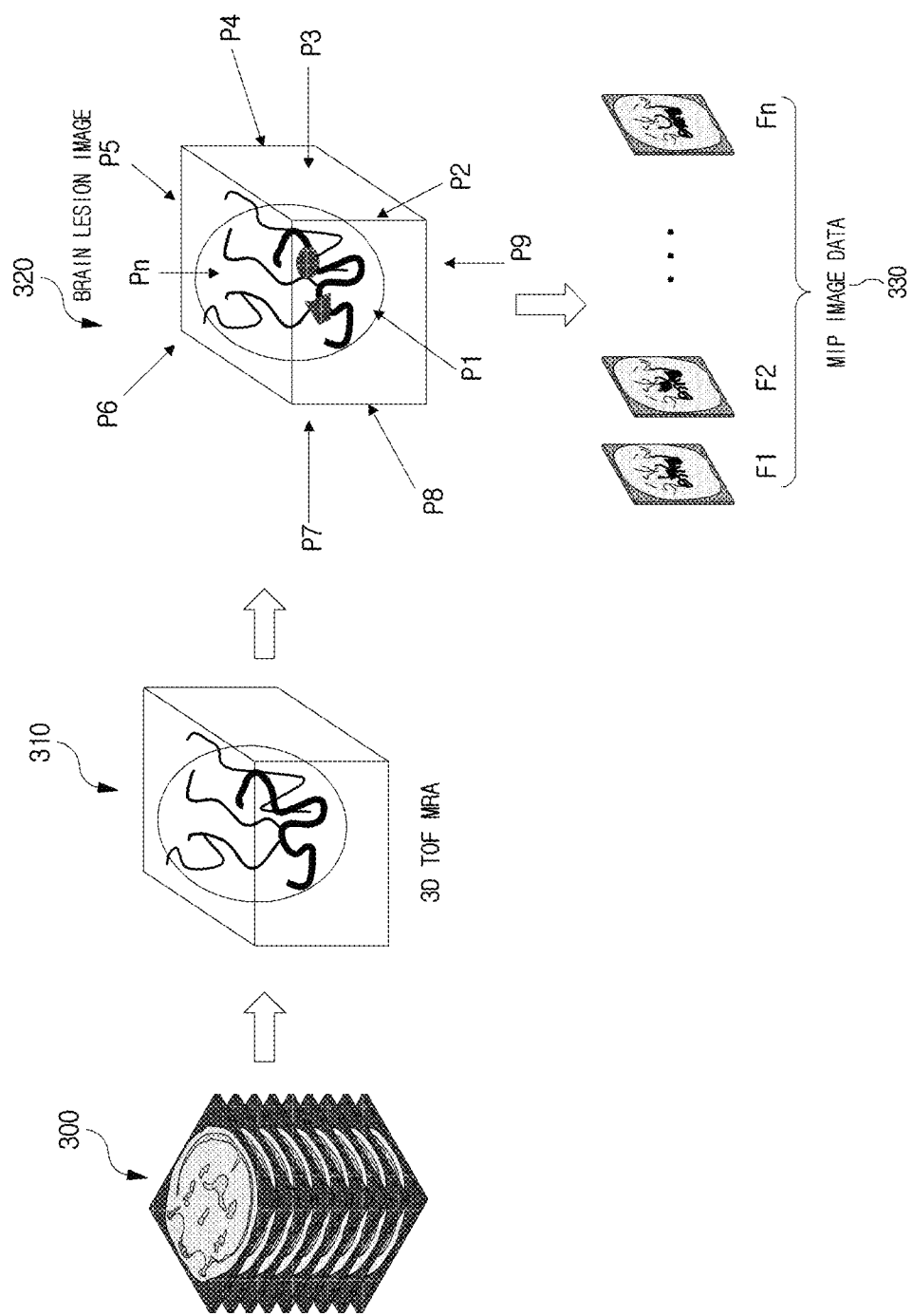
FIG. 3 is a view illustrating a brain lesion image and MIP image data configured in a brain lesion information provision apparatus according to an embodiment of the present disclosure.

For example, referring to FIG. 3, a brain lesion image 320 may be generated based on 3D TOF MRA 310 configured by stacking a plurality of 2D MRA images 300. In addition, at least one projection position may be set based on the brain lesion image. The MIP converter 15 may obtain and configure a first image frame F1 at a first projection position P1 and obtain and configure a second image frame F2 at a second projection position. The MIP converter 15 may obtain n image frames Fn corresponding to n projection positions Pn by repeatedly performing such operation. In addition, the MIP converter 15 may configure MIP image data 330 by aligning the n image frames Fn according to the predetermined position.

The noise remover 17 may extract brain lesion information from each of the image frames included in the MIP image data and check and remove noise of the extracted brain lesion information. For example, predetermined noise may be included in the brain lesion information extracted from each image frame. The noise remover 17 may remove noise, by performing processing such as dilation or erosion of the extracted brain lesion information. Furthermore, the noise remover 17 may remove noise, by applying a predetermined weight to a result of performing processing such as dilation or erosion of the extracted brain lesion information and performing weighted summation.

In addition, the noise remover 17 may configure corrected MIP image data 410 (see FIG. 4) by applying brain lesion information, from which noise is removed, to the MIP image data.

Detailed operation of the noise remover 17 for removing noise will be described in detail with reference to FIGS. 5a to 5c.

Meanwhile, the MRA reconfiguration unit 19 may reconfigure a 3D brain lesion image (hereinafter referred to as a "corrected brain lesion image") using the corrected MIP image data 410 provided by the noise remover 17. That is, the MRA reconfiguration unit 19 may configure a corrected brain lesion image 430 by back-projecting the corrected MIP image data 410 in consideration of a projection method used to configure the MIP image data based on the brain lesion image.

Hereinafter, detailed operation of the noise remover will be described with respect to FIGS. 5a to 5c.

Figure 5A:
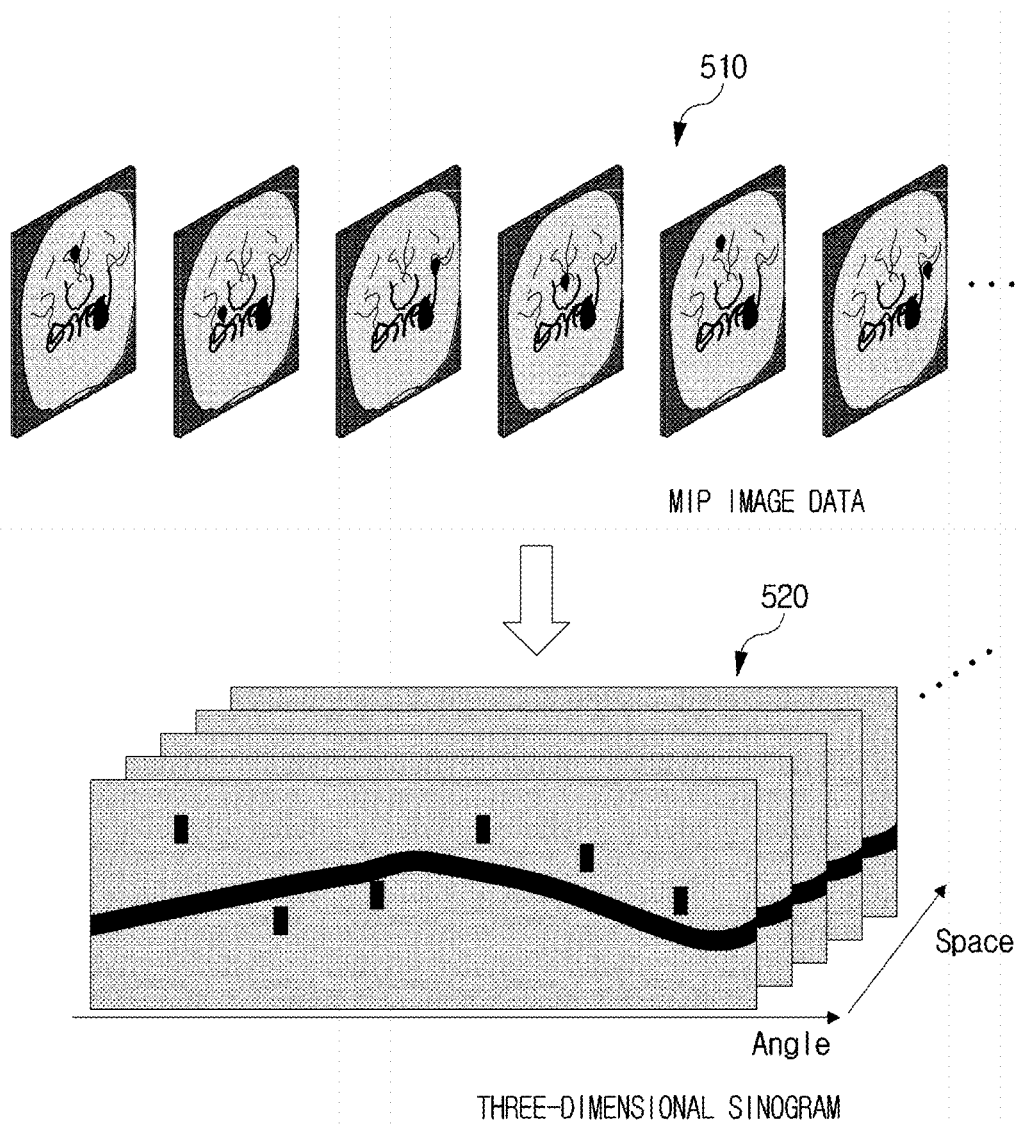
Figure 5C:
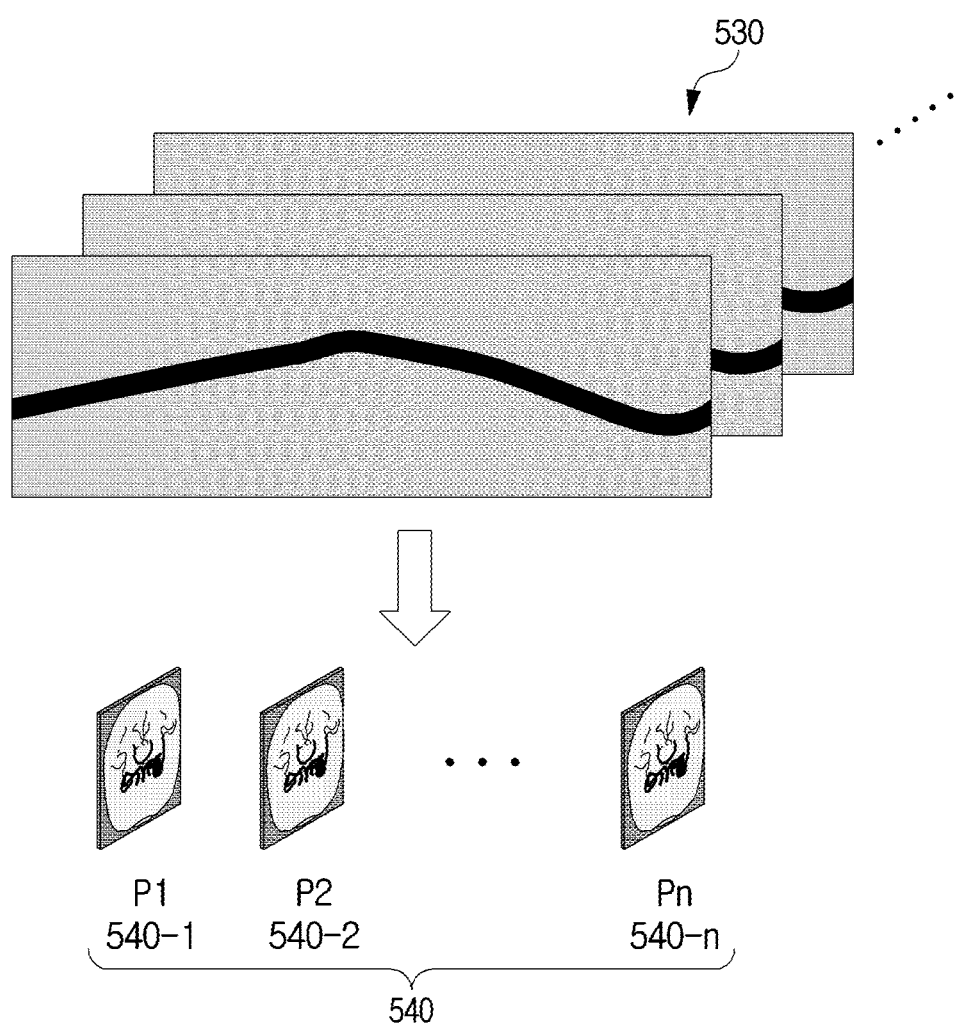

FIGS. 5a to 5c are views illustrating data processed by a noise remover provided in a brain lesion information provision apparatus according to an embodiment of the present disclosure. FIG. 5a shows a sinogram configured by a noise remover, FIG. 5b shows operation of performing noise removal using the sinogram, and FIG. 5c shows operation of configuring corrected MIP image data from a sinogram, from which noise is removed.

First, referring to FIG. 5a, since MIP image data 510 received from an MIP converter is configured based on a brain lesion image including brain lesion information, the noise remover 17 may detect brain lesion information, that is, a brain lesion area, from each image frame included in the MIP image data 510.

Thereafter, the noise remover 17 may reconfigure brain lesion information, that is, a brain lesion area, detected from each image frame into a three-dimensional sinogram 520.

Since the brain lesion information is input by a user using a user interface or is detected through a pre-trained brain lesion area learning model, there may be error or noise 521a, 521b and 521c (see FIG. 5b) of a brain lesion area. Accordingly, the noise remover 17 may perform processing such as dilation or erosion with respect to brain lesion information using a predetermined directional filter.

For example, the noise remover 17 may remove error or noise 521a, 521b and 521c of the brain lesion area by repeatedly performing processing dilation or erosion with respect to the three-dimensional sinogram 520. Furthermore, the noise remover 17 may perform error or noise removal through a weighted summation operation for applying a predetermined weight to a result of performing processing such as dilation or erosion with respect to the three-dimensional sinogram 520.

Through the above-described operation, the noise remover 17 may configure a sinogram, from which error or noise 521a, 521b and 521c present in the three-dimensional sinogram 520 is removed, that is, a corrected sinogram 530.

Thereafter, the noise remover 17 may check the corrected sinogram 530 corresponding to each image frame and apply the corrected sinogram 530 in consideration of the projection positions P1, P2, . . . Pn of the image frames, thereby configuring corrected MIP image data 540 (see FIG. 5c).

Meanwhile, in the above-described embodiment of the present disclosure, in the brain lesion input unit provided in the brain lesion information provision apparatus, the user inputs a brain lesion area.

As another example, the brain lesion input unit may detect and input a brain lesion area using a pre-trained brain lesion area learning model.

As another example, the brain lesion input unit may input a brain lesion area by combining a brain lesion area detected using the pre-trained brain lesion area learning model and a brain lesion area input by the user.

Hereinafter, an apparatus and operation for detecting a brain lesion area using a pre-trained brain lesion area learning model will be described in detail.

FIG. 6 is a block diagram illustrating the configuration of a cerebrovascular disease detection apparatus provided in a brain lesion information provision apparatus according to an embodiment of the present disclosure.

Referring to FIG. 6, the cerebrovascular disease detection apparatus 60 may include an MIP MRA configuration unit 61, a space characteristic detector 62, a frame characteristic detector 64 and a lesion characteristic detector 66.

The MIP MRA configuration unit 61 may receive 3D Time-of-flight magnetic resonance angiography (3D TOF MRA) and configure maximum intensity projection magnetic resonance angiography (MIP MRA). Here, 3D TOF MRA may be 3D MRA obtained by strongly measuring a signal of an area, in which a blood vessel is present, in a brain area. The MIP MRA may be moving image data configured by time-series combination of image frames obtained by projecting 3D TOF MRA in various directions.

For example, the MIP MRA configuration unit 61 may check a predetermined projection position and obtain an image frame corresponding to the checked projection position. In addition, the MIP MRA configuration unit 61 may configure moving image data by time-series combination of a plurality of image frames obtained through the above-described operation based on a predetermined time unit.

Figure 7:
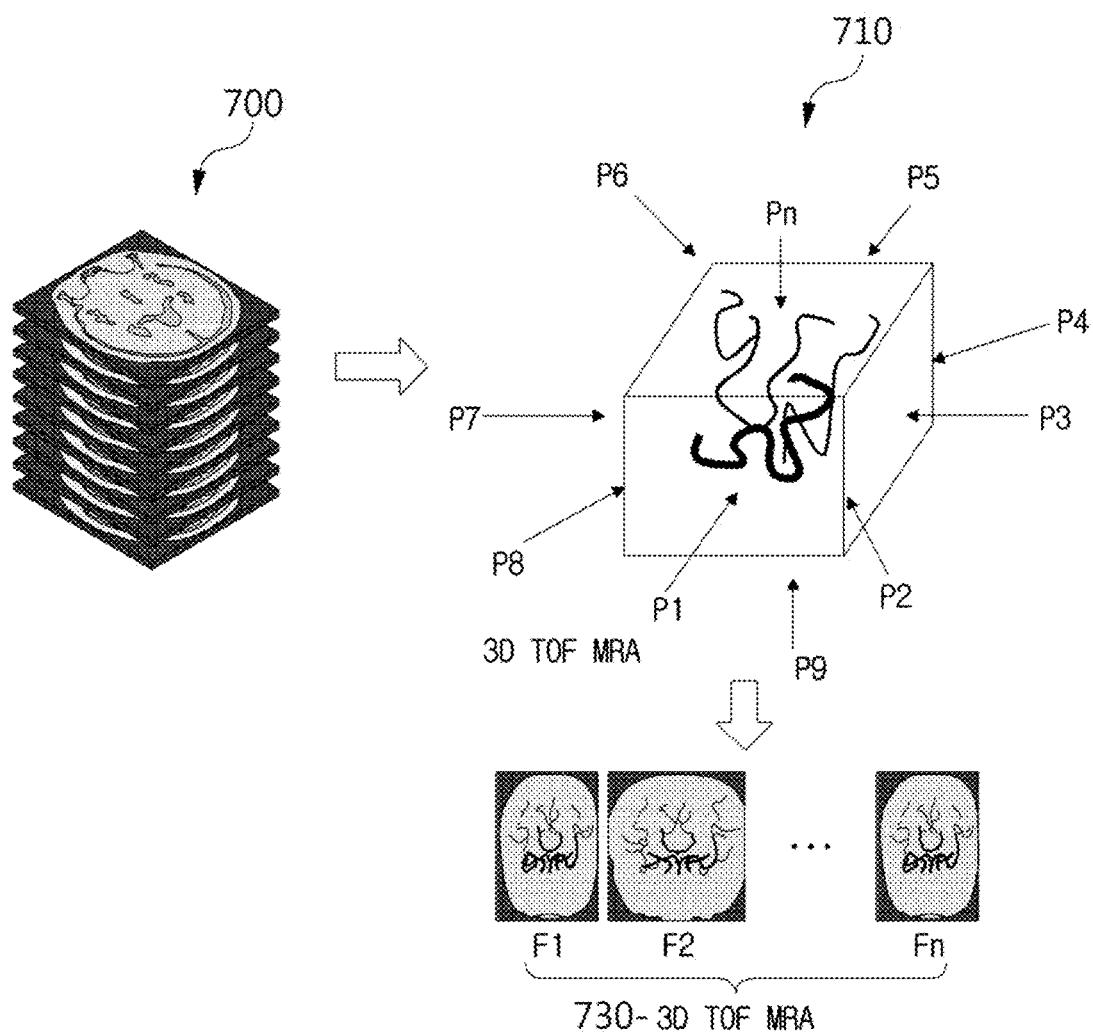
FIG. 7 is a view illustrating 3D TOF MRA and MIP MRA used in the cerebrovascular disease detection apparatus of FIG. 6.

For example, referring to FIG. 7, at least one projection position may be set based on 3D TOF MRA 710 configured by stacking a plurality of 2D MRA images 700. The MIP MRA configuration unit 61 may obtain and configure a first image frame F1 at a first projection position P1 and obtain and configure a second image frame F2 at a second projection position. The MIP MRA configuration unit 61 may obtain n image frames Fn corresponding to n projection positions Pn by repeatedly performing such operation. The MIP MRA configuration unit 61 may configure moving image data type MIP MRA 730 by aligning the n image frames Fn according to a predetermined position and arranging and combining the plurality of aligned images frames in predetermined time units (60 ms).

Furthermore, the MIP MRA may include projection positions P1, P2, . . . , Pn corresponding to image frames F1, F2, . . . , Fn and information on a time or arrangement order.

The space characteristic detector 62 may extract space characteristics from the image frames F1, F2, . . . , Fn included in the MIP MRA. In particular, the space characteristic detector 62 may include a space characteristic learning model 63 and extract space characteristics from the image frames F1, F2, . . . , Fn included in the MIP MRA through the space characteristic learning model 63.

For example, the space characteristic learning model 63 may include CNNs corresponding in number to the number of image frames F1, F2, . . . , Fn included in the MIP MRA, and the space characteristic detector 62 may transmit the first image frame F1 as input of a first CNN, transmit the second image frame F2 as input of a second CNN, and transmit an n-th image frame Fn as input of an n-th CNN.

In response thereto, a plurality of CNNs provided in the space characteristic learning model 63 may output a plurality of space characteristics respectively corresponding to the plurality of image frames F1, F2, . . . , Fn, and the space characteristic detector 62 may configure sequential data by sequentially arranging the plurality of space characteristics. At this time, the space characteristic detector 62 may configure sequential data in consideration of the projection positions P1, P2, . . . , Pn corresponding to the image frames F1, F2, . . . , Fn and information on a time or arrangement order.

Meanwhile, the frame characteristic detector 64 may receive a plurality of space characteristics composed of sequential data and detect characteristics (that is, frame characteristics) for a relationship between the image frames. Preferably, the frame characteristic detector 64 may detect frame characteristics using the frame characteristic learning model 65 based on a recurrent neural network (RNN) learning method.

Meanwhile, the lesion characteristic detector 66 may learn lesion information respectively corresponding to the plurality of image frames F1, F2, . . . , Fn. To this end, the frame characteristic detector 64 may configure parallel data by reconfiguring the frame characteristics composed of sequential data.

The lesion characteristic detector 66 may extract lesion characteristics from the frame characteristics received from the frame characteristic detector 64. In particular, the lesion characteristic detector 66 may include a lesion characteristic learning model 67.

The lesion characteristic learning model 67 may be a learning model based on a CNN learning method, and include CNNs corresponding in number to the number of image frames F1, F2, . . . , Fn included in the MIP MRA. In addition, the lesion characteristic detector 66 may be configured to transmit a first frame characteristic corresponding to the first image frame F1 as input of a first CNN, to transmit a second frame characteristic corresponding to the second image frame F2 as input of a second CNN, and to transmit a n-th frame characteristic corresponding to the n-th image frame Fn as input of an n-th CNN.

Furthermore, the plurality of CNNs provided in the space characteristic learning model 63 may include a pooling structure for reducing the size of an information extraction domain, and the plurality of CNNs provided in the lesion characteristic learning model 67 may include an upsampling structure for increasing the size of a domain of a feature map.

The plurality of CNNs provided in the space characteristic learning model 63 and the lesion characteristic learning model 67 preferably includes two 3×3 convolutions. In addition, the space characteristic learning model 63 may include a 2×2 max-pooling operation structure, and the lesion characteristic learning model 67 may include a structure for doubling a length and width by bilinear interpolation.

Although, in the embodiment of the present disclosure, the size and number of convolutions provided in the space characteristic learning model 63 and the lesion characteristic learning model 67, the pooling structure provided in the space characteristic learning model 63 and the upsampling structure are shown, the present disclosure is not limited thereto and various modifications are possible.

Figure 8:
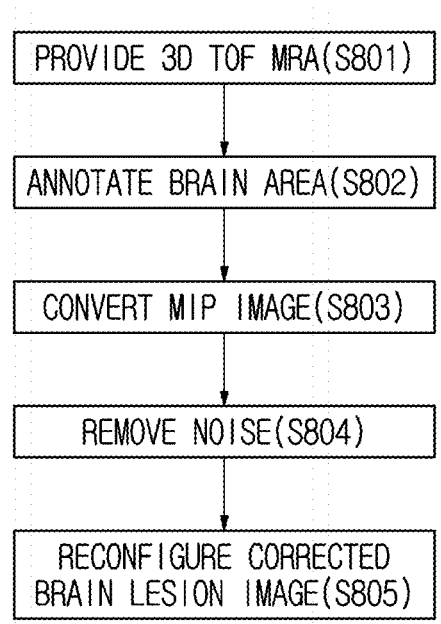
FIG. 8 is a flowchart illustrating a brain lesion information provision method according to an embodiment of the present disclosure.

FIG. 8 is a flowchart illustrating a brain lesion information provision method according to an embodiment of the present disclosure.

The brain lesion information provision method according to the embodiment of the present disclosure may be performed by the brain lesion information provision apparatus.

First, in step S801, the brain lesion information provision apparatus may provide an environment capable of displaying 3D Time-of-flight magnetic resonance angiography (3D TOF MRA) using user input. 3D TOF MRA may be 3D MRA obtained by strongly measuring a signal of an area, in which a blood vessel is present, in a brain area. Since 3D TOF MRA is 3D data, the brain lesion information provision apparatus may check an area input by a user and set a projection position according to the checked area.

For example, the brain lesion information provision apparatus may be connected to an external input device such as a mouse device, a digitizer device or a touchscreen device to check a signal input through the external input device. In addition, the brain lesion information provision apparatus may check a projection position corresponding to an input area of an external input device and display 3D TOF MRA appearing at a position corresponding thereto.

In step S802, the brain lesion information provision apparatus may annotate an area selected by a user as a brain lesion area while displaying 3D TOF MRA.

Specifically, the brain lesion information provision apparatus may provide a user interface capable of outputting 3D TOF MRA on a display and receiving an area in which a brain lesion is present, that is, a brain lesion area, in the output 3D TOF MRA, and annotate an area selected thereby as a brain lesion area.

The brain lesion information provision apparatus may store and manage the annotated brain lesion area as brain lesion information and, in particular, generate and manage a brain lesion image through combination with 3D MRA. The brain lesion image is based on 3D MRA, may be configured in a 3D form, and may be differently represented according to a projection position. Based on this, in step S803, the brain lesion information provision apparatus may convert a 3D brain lesion image into at least one maximum intensity projection (MIP) image corresponding to a predetermined projection position and provide the converted MIP image.

For example, the brain lesion information provision apparatus may check the predetermined projection position and obtain an image frame corresponding to the checked projection position from the brain lesion image. In addition, the brain lesion information provision apparatus may configure MIP image data by combining a plurality of image frames obtained through the above-described operation.

For example, referring to FIG. 3, a brain lesion image 320 may be generated based on 3D TOF MRA 310 configured by stacking a plurality of 2D MRA images 300. In addition, at least one projection position may be set based on the brain lesion image. The brain lesion information provision apparatus may obtain and configure a first image frame F1 at a first projection position P1 and obtain and configure a second image frame F2 at a second projection position. The MIP converter 15 may obtain n image frames Fn corresponding to n projection positions Pn by repeatedly performing such operation. In addition, the brain lesion information provision apparatus may configure MIP image data 330 by aligning the n image frames Fn according to the predetermined position.

In step S804, the brain lesion information provision apparatus may extract brain lesion information from each of the image frames included in the MIP image data and check and remove noise of the extracted brain lesion information.

Specifically, since MIP image data 510 (see 5a) is configured based on the brain lesion image including the brain lesion information, the brain lesion information provision apparatus may detect brain lesion information, that is, a brain lesion area, from each image frame included in the MIP image data 510.

Thereafter, the brain lesion information provision apparatus may reconfigure brain lesion information detected from each image frame, that is, a brain lesion area, as a three-dimensional sinogram 520.

Since the brain lesion information is input by a user using a user interface or is detected through a pre-trained brain lesion area learning model, there may be error or noise 521a, 521b and 521c (see FIG. 5b) of a brain lesion area. Accordingly, the brain lesion information provision apparatus may perform processing such as dilation or erosion with respect to brain lesion information using a predetermined directional filter.

For example, the brain lesion information provision apparatus may remove error or noise 521a, 521b and 521c of the brain lesion area by repeatedly performing processing dilation or erosion with respect to the three-dimensional sinogram 520.

Furthermore, the brain lesion information provision apparatus may perform error or noise removal through a weighted summation operation for applying a predetermined weight to a result of performing processing such as dilation or erosion with respect to the three-dimensional sinogram 520.

Through the above-described operation, the brain lesion information provision apparatus may configure a sinogram, from which error or noise 521a, 521b and 521c present in the three-dimensional sinogram 520 is removed, that is, a corrected sinogram 530.

Thereafter, the brain lesion information provision apparatus may check the corrected sinogram 530 corresponding to each image frame and apply the corrected sinogram 530 in consideration of the projection positions P1, P2, . . . , Pn of the image frames, thereby configuring corrected MIP image data 540 (see FIG. 5c).

Figure 4:
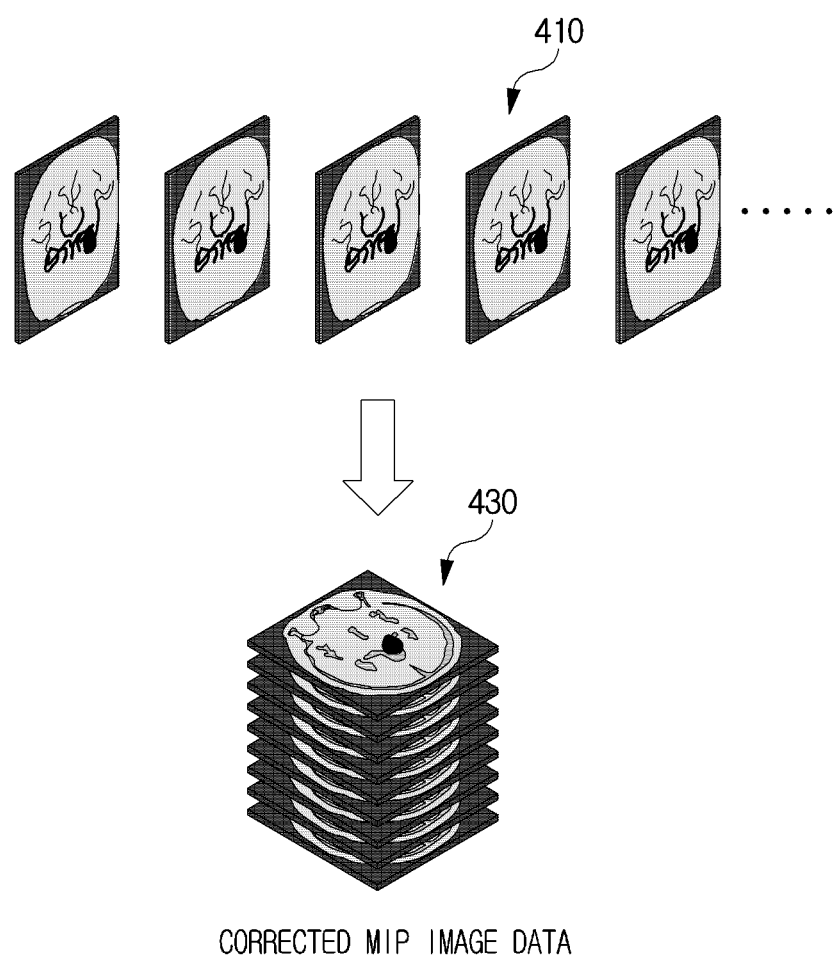
FIG. 4 is a view illustrating a corrected brain lesion image and corrected MIP image data configured in a brain lesion information provision apparatus according to an embodiment of the present disclosure.

Meanwhile, in step S805, the brain lesion information provision apparatus may reconfigure a 3D brain lesion image (hereinafter referred to as a "corrected brain lesion image") using the corrected MIP image data 410 (see FIG. 4). That is, the brain lesion information provision apparatus may configure a corrected brain lesion image 430 by back-projecting the corrected MIP image data 410 in consideration of a projection method used to configure the MIP image data based on the brain lesion image.

According to the present disclosure, it is possible to provide a method and apparatus capable of constructing a three-dimensional image accurately representing a brain lesion area detected using 3D TOF MRA in a three-dimensional structure.

According to the present disclosure, it is possible to provide a method and apparatus capable of accurately representing a brain lesion area on a three-dimensional image, by removing noise which may occur upon input.

It will be appreciated by persons skilled in the art that that the effects that can be achieved through the present disclosure are not limited to what has been particularly described herein and other advantages of the present disclosure will be more clearly understood from the detailed description.

Figure 9:
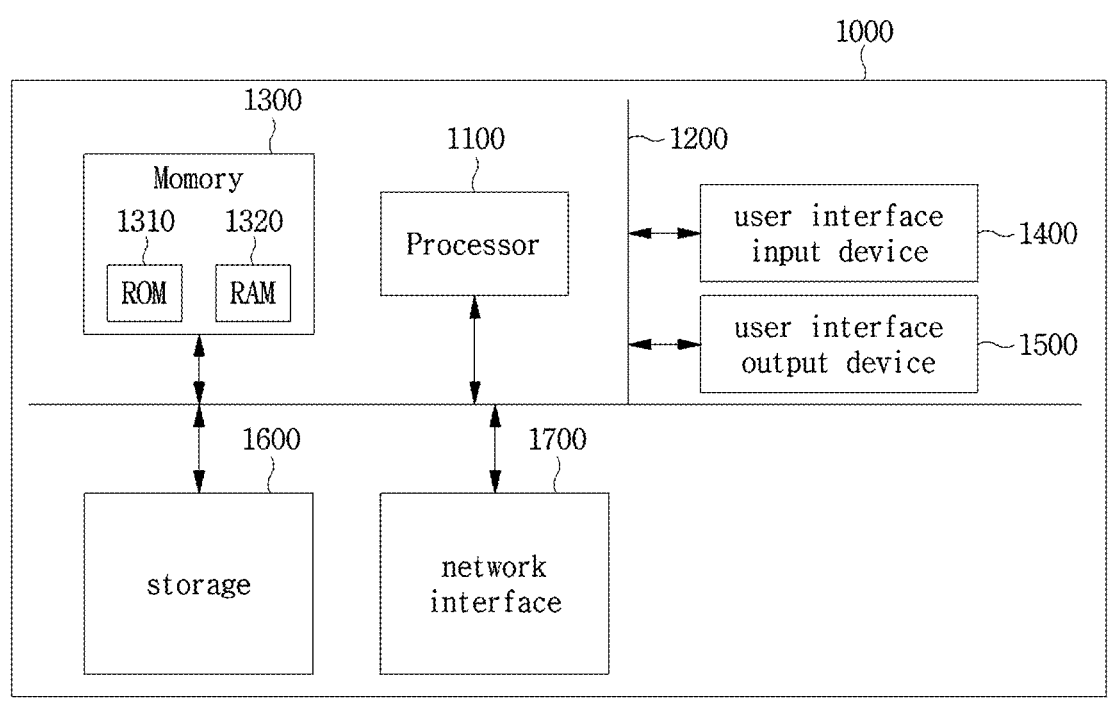
FIG. 9 is a block diagram illustrating a computing system for executing a brain lesion information provision apparatus and method according to an embodiment of the present disclosure.

FIG. 9 is a block diagram illustrating a computing system for executing a brain lesion information provision apparatus and method according to an embodiment of the present disclosure.

Referring to FIG. 9, a computing system 100 may include at least one processor 1100 connected through a bus 1200, a memory 1300, a user interface input device 1400, a user interface output device 1500, a storage 1600, and a network interface 1700.

The processor 1100 may be a central processing unit or a semiconductor device that processes commands stored in the memory 1300 and/or the storage 1600. The memory 1300 and the storage 1600 may include various volatile or non-volatile storing media. For example, the memory 1300 may include a ROM (Read Only Memory) and a RAM (Random Access Memory).

Accordingly, the steps of the method or algorithm described in relation to the embodiments of the present disclosure may be directly implemented by a hardware module and a software module, which are operated by the processor 1100, or a combination of the modules. The software module may reside in a storing medium (that is, the memory 1300 and/or the storage 1600) such as a RAM memory, a flash memory, a ROM memory, an EPROM memory, an EEPROM memory, a register, a hard disk, a detachable disk, and a CD-ROM. The exemplary storing media are coupled to the processor 1100 and the processor 1100 can read out information from the storing media and write information on the storing media. Alternatively, the storing media may be integrated with the processor 1100.

The processor and storing media may reside in an application specific integrated circuit (ASIC). The ASIC may reside in a user terminal. Alternatively, the processor and storing media may reside as individual components in a user terminal.

The exemplary methods described herein were expressed by a series of operations for clear description, but it does not limit the order of performing the steps, and if necessary, the steps may be performed simultaneously or in different orders. In order to achieve the method of the present disclosure, other steps may be added to the exemplary steps, or the other steps except for some steps may be included, or additional other steps except for some steps may be included.

Various embodiments described herein are provided to not arrange all available combinations, but explain a representative aspect of the present disclosure and the configurations about the embodiments may be applied individually or in combinations of at least two of them.

Further, various embodiments of the present disclosure may be implemented by hardware, firmware, software, or combinations thereof. When hardware is used, the hardware may be implemented by at least one of ASICs (Application Specific Integrated Circuits), DSPs (Digital Signal Processors), DSPDs (Digital Signal Processing Devices), PLDs (Programmable Logic Devices), FPGAs (Field Programmable Gate Arrays), a general processor, a controller, a micro controller, and a micro-processor.

The scope of the present disclosure includes software and device-executable commands (for example, an operating system, applications, firmware, programs) that make the method of the various embodiments of the present disclosure executable on a machine or a computer, and non-transitory computer-readable media that keeps the software or commands and can be executed on a device or a computer.

What is claimed is:

1. An electronic apparatus for providing brain lesion information based on an image, the electronic apparatus comprising:
   a magnetic resonance angiography (MRA) provider configured to provide an environment capable of displaying 3D time-of-flight magnetic resonance angiography (3D TOF MRA) using user input;
   a brain lesion input unit configured to annotate a brain lesion area and to generate and manage a brain lesion image by combining the annotated brain lesion area and the 3D TOF MRA;
   a maximum intensity projection (MIP) converter configured to configure MIP image data including at least one image frame corresponding to a projection position of the brain lesion image;
   a noise remover configured to configure at least one three-dimensional sinogram using the brain lesion image, remove noise of the at least one three-dimensional sinogram, and configure corrected MIP image data reflecting brain lesion information based on the noise-removed three-dimensional sinogram; and
   an MRA reconfiguration unit configured to reconfigure a corrected brain lesion image by back-projecting the corrected MIP image data.

2. The electronic apparatus of claim 1, wherein the brain lesion input unit detects and sets the brain lesion area using a pre-trained brain lesion area learning model.

3. The electronic apparatus of claim 1, wherein the noise remover is
   configured to apply at least one predetermined filter to the at least one three-dimensional sinogram, to apply dilation or erosion to the at least one predetermined filter, and to remove error or noise of the brain lesion information by reflecting a result of application.

4. The electronic apparatus of claim 3, wherein the noise remover is configured to remove error or noise of the brain lesion information by performing weighted summation operation with respect to a result of filtering the at least one three-dimensional sinogram.

5. The electronic apparatus of claim 1, wherein the brain lesion input unit is configured to provide an environment, in which a user is able to annotate the brain lesion area, and receives and sets the brain lesion area from the user.

6. The electronic apparatus of claim 5, wherein the brain lesion input unit detects and sets the brain lesion area using a pre-trained brain lesion area learning model.

7. A method of, by an electronic apparatus, providing brain lesion information based on an image, the method comprising:
   providing 3D time-of-flight magnetic resonance angiography (3D TOF MRA);
   annotating a brain lesion area and generating a brain lesion image by combining the annotated brain lesion area and the 3D TOF MRA;
   configuring maximum intensity projection (MIP) image data including at least one image frame corresponding to a projection position of the brain lesion image;
   configuring corrected MIP image data by configuring at least one three-dimensional sinogram using the brain lesion image, removing noise of the at least one three-dimensional sinogram, and configuring the corrected MIP image data reflecting brain lesion information based on the noise-removed three-dimensional sinogram; and
   reconfiguring a corrected brain lesion image by back-projecting the corrected MIP image data.

8. The method of claim 7, wherein the removing the error or noise of the brain lesion information comprises applying at least one predetermined filter to the at least one three-dimensional sinogram, applying dilation or erosion to the at least one predetermined filter, and
   removing error or noise of the brain lesion information by reflecting a result of application.

9. The method of claim 8, wherein the removing the error or noise of the
   brain lesion information comprises removing error or noise of the brain lesion information by performing weighted summation operation with respect to a result of filtering the at least one three-dimensional sinogram.

10. The method of claim 7, wherein the generating the brain lesion image comprises:
    receiving a brain lesion area from a user and setting the brain lesion area or detecting and setting the brain lesion area using a pre-trained brain lesion area learning model.

* * * * *